US012648698B2

(12) United States Patent
Kwack et al.

(10) Patent No.: US 12,648,698 B2
(45) Date of Patent: Jun. 9, 2026

(54) OPTOGENETIC NEURAL PROBE DEVICE WITH PLURALITY OF INPUTS AND OUTPUTS AND METHOD OF MANUFACTURING THE SAME

(71) Applicant: ELECTRONICS AND TELECOMMUNICATIONS RESEARCH INSTITUTE, Daejeon (KR)

(72) Inventors: Myungjoon Kwack, Daejeon (KR); Jaegyu Park, Daejeon (KR); Hyung Ju Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 18/672,674

(22) Filed: May 23, 2024

(65) Prior Publication Data

US 2024/0407650 A1 Dec. 12, 2024

(30) Foreign Application Priority Data

Jun. 7, 2023 (KR) ........................ 10-2023-0072831

(51) Int. Cl.
*A61B 5/00* (2006.01)
(52) U.S. Cl.
CPC ........ *A61B 5/0071* (2013.01); *A61B 2503/42* (2013.01)
(58) Field of Classification Search
CPC .. A61B 5/0071; A61B 2503/42; A61N 5/0601
See application file for complete search history.

(56) References Cited

U.S. PATENT DOCUMENTS 6,091,874 A * 7/2000 Higashi ................ G02B 6/1221
385/132
10,471,273 B2 11/2019 Segev et al.
10,638,933 B2 5/2020 Roukes
(Continued)

FOREIGN PATENT DOCUMENTS

JP 2019-95565 A 6/2019
KR 10-1828149 B1 2/2018
(Continued)

OTHER PUBLICATIONS

Anthony N. Zorzos, et al., "Three-dimensional multiwaveguide probe array for light delivery to distributed brain circuits", Optics Letters, vol. 37, No. 23, Dec. 1, 2012, pp. 1-3.

*Primary Examiner* — Adam Z Minchella
(74) *Attorney, Agent, or Firm* — Sughrue Mion, PLLC

(57) ABSTRACT

An optogenetic neural probe device for transmitting an optical signal to a nerve cell or receiving a fluorescent signal from the nerve cell, including: an optical device alignment substrate; an optical device group on the optical device alignment substrate and including one or more optical devices; and one or more optogenetic neural probes, wherein each optogenetic neural probe from among the one or more optogenetic neural probes may include an optical neural probe substrate, an optical waveguide on the optical neural probe substrate, and an optical signal input/output port, wherein the optogenetic neural probe is configured to transmit the optical signal emitted from the optical device group to the optical signal input/output port through the optical waveguide.

16 Claims, 13 Drawing Sheets

(56) References Cited

U.S. PATENT DOCUMENTS

| | | | |
|---|---|---|---|
| 10,649,139 B2 | 5/2020 | Kim et al. | |
| 11,045,076 B2 | 6/2021 | Kim et al. | |
| 11,589,764 B1 * | 2/2023 | Davis ................... | A61B 5/0537 |
| 2010/0234793 A1 * | 9/2010 | Dacey, Jr. ............ | A61N 5/0601 |
| | | | 604/8 |
| 2012/0089205 A1 * | 4/2012 | Boyden ............... | A61N 5/0601 |
| | | | 607/88 |
| 2015/0018901 A1 * | 1/2015 | Li ........................ | A61N 5/0622 |
| | | | 607/92 |
| 2016/0150963 A1 * | 6/2016 | Roukes ............... | A61B 5/4029 |
| | | | 600/476 |
| 2018/0028119 A1 | 2/2018 | Jamieson et al. | |
| 2021/0085996 A1 | 3/2021 | Cho et al. | |
| 2024/0424317 A1 * | 12/2024 | Sfez .................... | A61N 5/0601 |

FOREIGN PATENT DOCUMENTS

| | | | |
|---|---|---|---|
| KR | 10-2021-0033776 A | 3/2021 |
| WO | 2022/162526 A1 | 8/2022 |

* cited by examiner

OPTOGENETIC NEURAL PROBE DEVICE WITH PLURALITY OF INPUTS AND OUTPUTS AND METHOD OF MANUFACTURING THE SAME

CROSS-REFERENCE TO RELATED APPLICATION

This application claims priority under 35 U.S.C. § 119 to Korean Patent Application No. 10-2023-0072831, filed on Jun. 7, 2023, in the Korean Intellectual Property Office, the disclosure of which is incorporated herein by reference in its entirety.

BACKGROUND

1. Field

The disclosure relates to a neural probe device configured to stimulate and inhibit nerve cells, and to extract nerve signals using optogenetic technology, and a method of manufacturing the neural probe device.

2. Description of Related Art

In general, signal transmission in nerve cells occurs through electrochemical actions. Therefore, a direct electrical stimulation technique may be used to artificially activate nerves, for example by placing an electrode in proximity to a nerve cell and applying an appropriate amount of current or voltage has been used. Furthermore, it is possible to artificially activate nerves not only by light stimulation but also by electrical stimulation by transplanting proteins, such as channelrhodopsin-2 (ChR2), that acts as a light-sensitive ion channel, into a nerve cell and irradiating the protein with light having a specific wavelength. These and other techniques for stimulating or inhibiting specific types of nerves using light may be referred to as optogenetic techniques. Using the direct electrical stimulation technique, it is impossible to determine the role of each nerve in a living organism, but optogenetic techniques may be used to investigate the roles of nerves at the cell level using optogenetic technology, which may provide a new perspective in the field of neural research.

Some optogenetic techniques may include placing a light emitting surface of a light source in proximity to a nerve cell being studied, or connecting an external light source to an optical fiber and placing the end of the optical fiber in proximity to a nerve cell using the optical fiber as a medium, and directing light to the nerve. However, general external light sources are often very large, and may require a complex combination of optical systems to reduce the illumination area. Therefore, the overall volume of the optical system may increase, making it is difficult to insert the optical system into living organisms. In addition, optical fibers have limitations in the processing methods thereof, and it may be difficult to transmit light to areas other than the end of the optical fiber due to its structure, which may cause difficulties when studying neural tissue having a three-dimensional structure in which numerous cells are present in bundles.

Efforts to resolve the above issues include techniques for integrating relatively small light emitters, such as micro light emitting diodes (mLEDs), into a probe-type electrode, and inserting the light emitters into neural tissue in proximity to a target nerve cell. However, these techniques may use a separate light source for each part that is to be illuminated, and the light sources may be located in an area directly adjacent to a nerve cell, which may increase the risk of thermal damage to the nerve cell or the surrounding neural tissue.

SUMMARY

Provided is an optogenetic neural probe device having a plurality of inputs and outputs based on optogenetic neural probe manufacturing technology using an optical semiconductor device process, and a method of manufacturing the same.

Also provided is an optogenetic neural probe device which has a plurality of inputs and outputs and which has an independent optical device array chip as a base to enable physical separation between a light source and biological tissue, and which employs a probe array based on optical waveguide technology having structural scalability in design and manufacturing to achieve optical signal input and output suitable for research on neural tissue having a three-dimensional volume, and a method of manufacturing the same.

Additional aspects will be set forth in part in the description which follows and, in part, will be apparent from the description, or may be learned by practice of the presented embodiments.

In accordance with an aspect of the disclosure, an optogenetic neural probe device for transmitting an optical signal to a nerve cell or receiving a fluorescent signal from the nerve cell includes: an optical device alignment substrate; an optical device group on the optical device alignment substrate and including one or more optical devices; and one or more optogenetic neural probes, wherein each optogenetic neural probe from among the one or more optogenetic neural probes may include an optical neural probe substrate, an optical waveguide on the optical neural probe substrate, and an optical signal input/output port, wherein the optogenetic neural probe is configured to transmit the optical signal emitted from the optical device group to the optical signal input/output port through the optical waveguide.

The optical device group may include a first optical device and a second optical device, and a central wavelength characteristic of the first optical device may be different from a central wavelength characteristic of the second optical device.

The optical device group may include a first optical device and a second optical device, the first optical device may include a light emitting element, and the second optical device may include a light receiving element.

The optical signal input/output port may be configured to transmit the fluorescent signal of the nerve cell to the optical waveguide, and the optical waveguide may be configured to transmit the fluorescent signal of the nerve cell to the optical device group.

The optical neural probe substrate may be packaged on one side of the optical device alignment substrate.

The optogenetic neural probe may include a plurality of shanks, each shank from among the plurality of shanks may include a protrusion of the optical neural probe substrate, the optical waveguide, and the optical signal input/output port, and the plurality of shanks may be spaced apart from each other at a predetermined interval.

The optical neural probe substrate may directly contact the optical device group at a portion of the optical neural probe substrate that is packaged on the optical device alignment substrate, the portion may include a recess structure including a step, and a height of the step may be equal to a height of the optical device group.

The optical device alignment substrate may be coated with a fixing resin such that the optical neural probe substrate is fixed to the optical device alignment substrate.

The fixing resin may include at least one from among a thermosetting resin and a photocurable resin.

The optical signal input/output port may be disposed at an end of the optical waveguide.

At least one shank from among the plurality of shanks may include a plurality of optical signal input/output ports on the optical waveguide included in the at least one shank.

At least one shank from among the plurality of shanks may include a plurality of optical waveguides.

The optical signal input/output port may include a diffraction grating.

The optical signal input/output port may include a 45 degree mirror surface.

The optical device group may include a plurality of optical device groups.

In accordance with an aspect of the disclosure, a method of manufacturing an optogenetic neural probe device includes: arraying a plurality of optogenetic neural probes using a fixing spacer; placing the plurality of optogenetic neural probes on an optical device alignment substrate on which a plurality of optical device groups are disposed; coating portions of a surface of the optical device alignment substrate contacting the plurality of optogenetic neural probes with a liquid fixing resin; and curing the fixing resin.

Each optogenetic neural probe from among the plurality of optogenetic neural probes may include an optical neural probe substrate, an optical waveguide on the optical neural probe substrate, and an optical signal input/output port, an end of the optical neural probe substrate may include a recess structure, and the positioning of the plurality of optogenetic neural probes may include placing the recess structure in contact with a corresponding optical device group from among the plurality of optical device groups and the optical device alignment substrate.

BRIEF DESCRIPTION OF DRAWINGS

The above and other objects, features and advantages of certain embodiments of the present disclosure will become more apparent from the following description taken in conjunction with the accompanying drawings, in which:

FIGS. 1A and 1B are front views illustrating an optogenetic neural probe device and an optogenetic neural probe having a plurality of inputs and outputs, according to embodiments;

FIG. 6 is an exemplary diagram illustrating an optogenetic neural probe having a plurality of inputs and outputs, which includes an optical switch, according to embodiments.

DETAILED DESCRIPTION

Figure 1A:
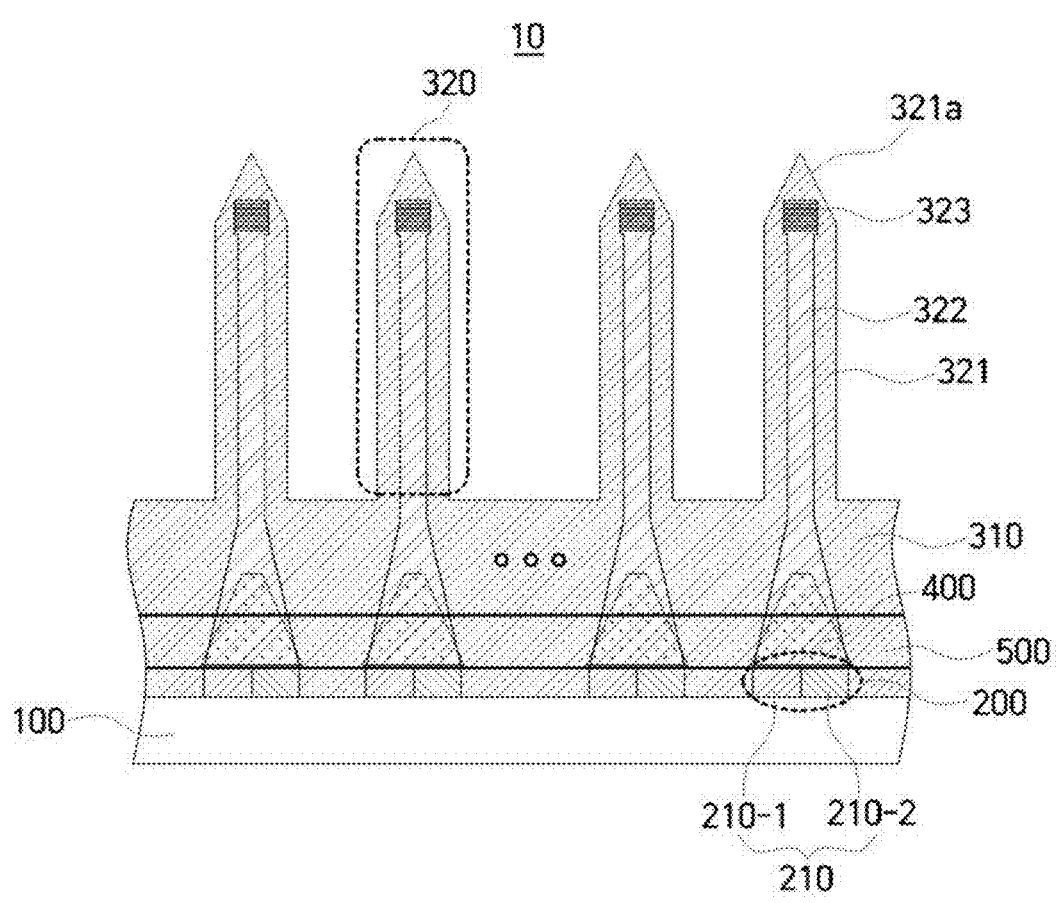

The embodiments described herein are non-limiting example embodiments, and thus, the disclosure is not limited thereto and may be realized in various other forms. The present disclosure relates to an optogenetic neural probe device that stimulates or inhibits nerve cells and extracts nerve signals using optogenetic technology, and a method of manufacturing the same.

For example, embodiments of the present disclosure may target nerve bundles having a three-dimensional volume and achieve connection with nerves at a specific location. The present disclosure relates to an optogenetic neural probe device including a plurality of optical device array chips that are optically connected to a plurality of optical neural probe arrays that are configured to transmit an optical signal generated from the array chip to a specific nerve region, or to receive a fluorescent signal generated in the brain and then transmit the fluorescent signal to the optical device array chip, and a method of manufacturing the same.

Advantages and features certain embodiments of the present disclosure and ways to achieve them will be more apparent with reference to the following detailed description of embodiments in conjunction with the accompanying drawings. The present disclosure is not limited to the embodiments described below, and may be embodied in various forms. Terms used herein are intended to aid in the explanation of various embodiments of the present disclosure, and are not intended to limit the scope and spirit of the present disclosure. It should be understood that singular forms also include plural forms unless the indicated otherwise. The terms "comprise," "comprising," "include," and/or "including" used herein specify the presence of stated components, steps, operations and/or elements and do not preclude the presence or addition of one or more other components, steps, operations and/or elements.

In the present disclosure, terms such as "first" and "second" are used only for the purpose of describing various components, and the components are not limited by the above terms. Terms such as "first" and "second" are used only for the purpose of distinguishing one component from another component. For example, without departing from the scope of the present disclosure, a first component may be referred to as a second element, and a second component may be referred to as a first element.

It will be understood that when a first component is referred to as being "connected" or "coupled" to a second component, this may mean that the first component is directly connected or coupled to the second components, or that intervening components may be present therebetween. When the first component is referred to as being "directly connected" or "directly coupled" to the second component, this may mean that there are no intervening components therebetween. Other words used to describe the relationship between components should be interpreted in a similar fashion (i.e., "between" versus "directly between," "adjacent" versus "directly adjacent," etc.).

In the description embodiments presented herein, detailed descriptions of related known technologies may be omitted when it is determined that they may unnecessarily obscure the embodiments of the present disclosure.

Hereinafter, embodiments are described in detail with reference to the accompanying drawings. In the drawings, some parts may be omitted for the clarity of explanation, and like numbers may generally refer to like elements throughout the description of the drawings.

Figure 1B:
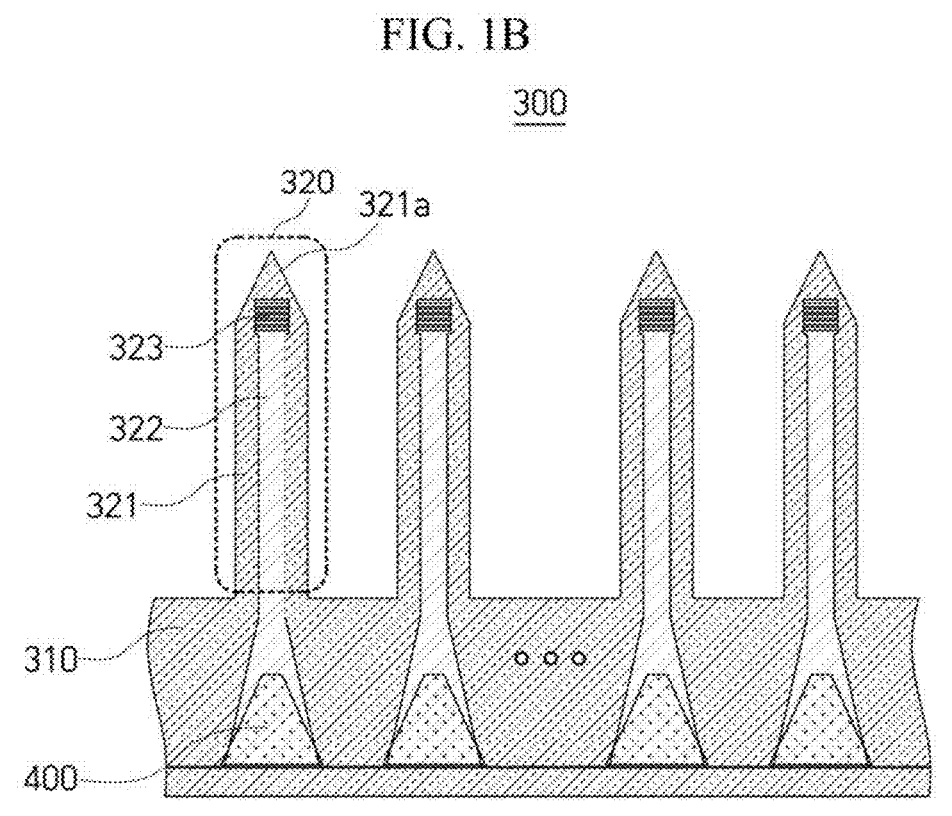

FIGS. 1A and 1B are front views illustrating an embodiment of an optogenetic neural probe device and an optogenetic neural probe having a plurality of inputs and outputs according to embodiments.

Referring to FIGS. 1A and 1B, examples of an optogenetic neural probe device and an optogenetic neural probe according to embodiments are described below.

The optogenetic neural probe device 10 may be used to study neural tissue having a three-dimensional volume by adopting a probe array structure including an optical waveguide. The optogenetic neural probe device 10 may include an optical device alignment substrate 100, one or more optical devices 210 (e.g., a first optical device 210-1 and a second optical device 210-2), which may be grouped into one or more optical device groups 200, and a probe 300, which may be for example an optogenetic neural probe, and may further include an optical mode size converter 400.

The probe 300 may include an optical neural probe substrate 310, one or more waveguides 322, which may be for example optical waveguides, and one or more optical signal input/output ports 323. In some embodiments, the optical mode size converter 400 may be further included in the probe 300 (as shown for example in FIG. 1B). The optical mode size converter 400 may be provided between the one or more optical devices (e.g., one or more light emitters) 210 and the waveguide 322, wherein a cross-section area size of the optical mode size converter 400 may decrease in a direction from the one or more optical devices 210 toward the optical signal input/output port 323. The optical signal input/output port 323 may be configured to output an optical signal to an object (e.g., a nerve cell) and receive a response signal (e.g., a fluorescent signal) from the object as a result of stimulation of the nerve cell caused by the optical signal.

In embodiments, a configuration including a protrusion 321 of the optical neural probe substrate 310, the waveguide 322 disposed on the protrusion 321, and the optical signal input/output port 323, may be referred to as a shank 320. Accordingly, the probe 300 may include one or more shanks 320. The number or location of the waveguides 322 and the optical signal input/output ports 323 included in each of the shanks 320 may vary for each shank 320. A portion of the optical neural probe substrate 310 excluding the protrusion 321 may be referred to as a substrate portion.

In some embodiments, the probe 300 may further include an optical switch 330.

In some embodiments, an electrode capable of receiving, or configured to receive, an electrophysiological signal generated from a nerve may be integrated into the shank 320. The electrode may be provided as one or more electrodes, similar to the optical signal input/output port 323, and each of the electrodes may transmit the collected nerve signals to a circuit, terminal, or system in which the signal may be analyzed through an electrical method or wireless communication.

In some embodiments, an end of the protrusion 321 adjacent to the nerve cell may have a sharp or sharpened structure, which may be referred to as a probe peak portion 321a, to facilitate insertion.

Various types of optical devices 210 or optical device groups 200 may be disposed on the optical device alignment substrate 100. As shown in FIG. 1A, the optical device groups 200 including the first optical device 210-1 and the second optical device 210-2 may be arranged adjacent to each other or spaced apart from each other by a predetermined distance on the optical device alignment substrate 100. According to embodiments, when the optical device group 200 includes a plurality of optical devices 210, the optical devices 210 may be distinguished from each other by being designated with different reference numerals such as 210-1, 210-2, . . . , and 210-n.

The optical device 210 disposed on the optical device alignment substrate 100 may be, or may include, at least one of a light emitting element and a light receiving element. For example, the optical device 210 may include a light emitting element such as a light emitting diode (LED), a micro-LED, a mini-LED, an organic LED (OLED), a laser diode (LD), and a vertical-cavity surface emitting laser (VCSEL). As another example, the optical device 210 may include a light receiving element such as a silicon photodiode (Si PD), a germanium photodiode (Ge PD), and an avalanche photodiode (APD).

As shown in FIG. 1A, two or more adjacent optical devices 210-1, 210-2, . . . , and 210-n, and the like may form, or may be included in, the optical device group 200, and a plurality of optical device groups 200 may be arranged and spaced apart from each other by a predetermined interval (e.g., the same interval) and disposed on the optical device alignment substrate 100. As another example, a plurality of optical device groups 200 may be disposed at irregular intervals on the optical device alignment substrate 100. In some embodiments, the optical devices 210 may be individually disposed at regular intervals or at irregular intervals on the optical device alignment substrate 100. In some embodiments, the arrangement of the plurality of optical devices 210-1, 210-2, . . . , and 210-n included in the optical device group 200 may vary from one optical device group 200 to another optical device group 200.

In an example optogenetic neural probe device 10 in which each of the optical device groups 200 includes two optical devices 210, the first optical device 210-1 and the second optical device 210-2 may have different functions or different characteristics. For example, the first optical device 210-1 and the second optical device 210-2 may both be micro-LED light emitting elements, and may have different central wavelength characteristics. As another example, the first optical device 210-1 may be a VCSEL light emitting element, and the second optical device 210-2 may be a Si PD light receiving element. In other example optogenetic neural probe devices 10 in which each optical device group includes three or more optical devices 210, each of the optical devices 210 included in a particular optical device group 200 may have different functions or characteristics.

The optical neural probe substrate 310 may be packaged on the optical device alignment substrate 100 in a direction that is perpendicular to an extension direction of the optical device alignment substrate 100. The optical neural probe substrate 310 may be packaged on the optical device alignment substrate 100 using a fixing resin 500. Because the optical neural probe substrate 310 may be included in the probe 300, the probe 300 may be described as being packaged on the optical device alignment substrate 100.

The optical neural probe substrate 310 may include an Si-based material having a relatively high physical strength. However, the material of the optical neural probe substrate 310 is not limited to the specific example described above (e.g., the Si-based material). The optical neural probe substrate 310 may support the waveguide 322 on the optical neural probe substrate 310 such that the waveguide 322 may transmit light emitted by the optical device 210 to a target nerve cell. For example, the waveguide 322 may be present on the optical neural probe substrate 310, and an optical signal emitted from the optical device 210 may pass through the inside of the waveguide 322 and reach the target nerve cell through the optical signal input/output port 323. In FIGS. 1A, 1B, 2A, and 2B, a single optical signal input/output port 323 is illustrated as being disposed at an end of each waveguide 322, but embodiments are not limited thereto, and there is no limitation on the position or number of optical signal input/output ports 323 disposed on the waveguide 322. In embodiments, the optical signal input/output port 323 may be disposed at any position on the waveguide 322, and any number of optical signal input/output ports 323 may be disposed on the waveguide 322. For example, the optical signal input/output port 323 may be disposed at the end of the waveguide 322, and may also be disposed at a portion other than the end of the waveguide 322.

Figure 2A:
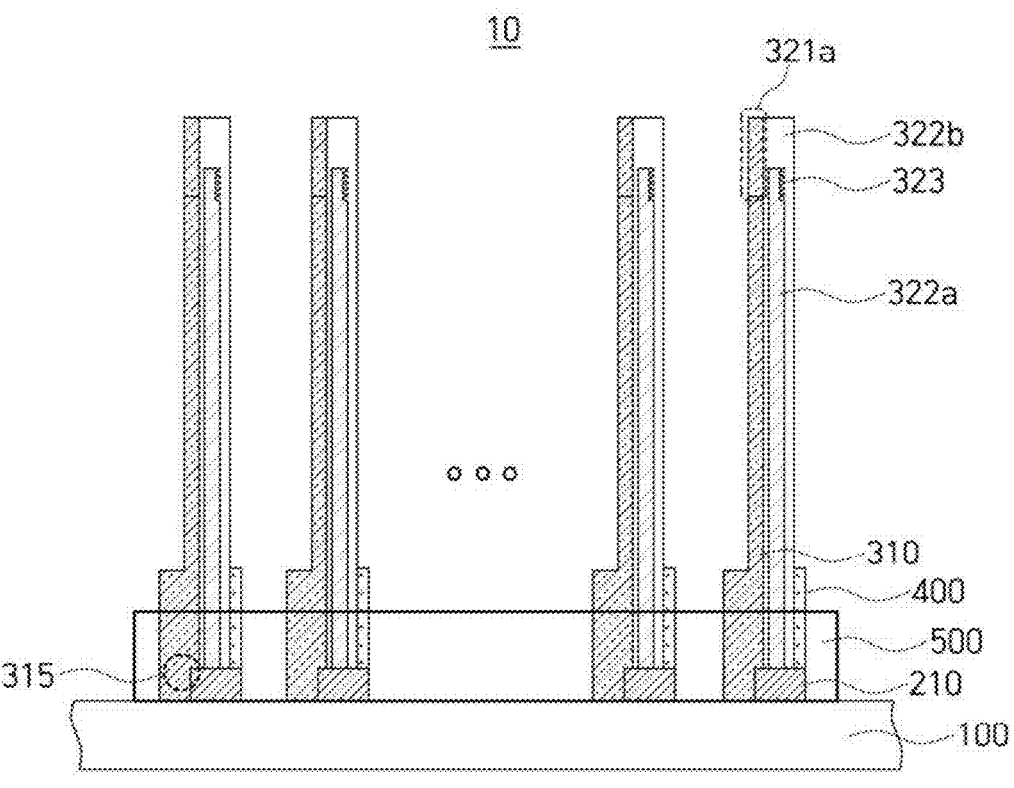
FIGS. 2A and 2B are side views illustrating an optogenetic neural probe device and an optogenetic neural probe having a plurality of inputs and outputs, according to embodiments.
Figure 2B:
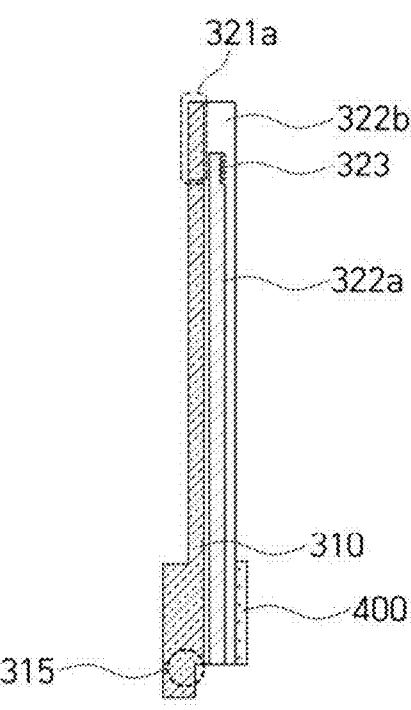

The waveguide 322 may include a core portion 322a and a cladding layer 322b (as shown for example in FIGS. 2A and 2B). Unless otherwise specified, references to the waveguide 322 may refer to the core portion 322a.

In embodiments, the core portion 322a may include a high refractive index material that may transmit visible light, and may include a material displaying a refractive index greater than or equal to 1.48. For example, the core portion 322a may include silicon nitride (SiN), silicon dioxide (SiO_2$), silicon oxynitride (SiON), a polymer, SU-8, parylene, and the like. However, the material of the core portion 322a is not limited to the specific examples described above.

Some or all of the core portion 322a may be exposed to air. In some embodiments, in order to reduce optical propagation loss, the core portion 322a may be fully or partially surrounded by the cladding layer 322b. The cladding layer 322b shown in FIGS. 2A and 2B may surround the core portion 322a. As shown in FIGS. 2A and 2B, the cladding layer 322b may be located between the core portion 322a and the optical mode size converter 400 and disposed between the optical neural probe substrate 310 and the core portion 322a. For example, the cladding layer 322b may include at least one from among SiN, SiO_2$, SiON, a polymer, PDMA, SU-8, parylene, and the like. In some embodiments, the material of the cladding layer 322b may have a refractive index lower than a refractive index of the material of the core portion 322a. However, the material of the cladding layer 322b is not limited to these specific examples.

Referring to FIG. 2A, the optical mode size converter 400 may be disposed on an upper side of the optical device 210. The optical mode size converter 400 may be located in or near an area in which the optical neural probe substrate 310 and the optical device alignment substrate 100 are connected. The optical mode size converter 400 may address or otherwise compensate for a difference in optical mode size between the waveguide 322 and the optical device group 200.

According to embodiments, when light is delivered to a target point through a medium such as an optical waveguide or optical fiber, the spatial shape (e.g., a size and pattern) of light trapped in the medium may vary depending on the refractive index or design characteristics of the material or materials included in the medium. Here, the spatial shape of light may be referred to as an "optical mode." In an active optical device (e.g., a light emitting element), such as a laser, the size of the optical mode, which may be referred to as the mode size or the optical mode size, of the emitted light may vary depending on the structure or direction of light amplification. The optical mode size converter 400 may be used to overcome or otherwise compensate for the difference in optical mode size between the optical device 210 and the waveguide 322.

The optical mode size converter 400 may adjust the optical mode size of the optical signal transmitted between the optical device 210 and the waveguide 322.

For example, when the optical device group 200 is disposed on the optical device alignment substrate 100, the optical mode size converter 400 may adjust the optical mode size of the optical signal transmitted between the optical device group 200 and the waveguide 322.

For example, when the optical device group 200 emits an optical signal, the optical mode size converter 400 may adjust the optical mode size of the optical signal emitted by the optical device group 200 such that the optical mode size of the emitted optical signal is closer to the optical mode size of the waveguide 322. In embodiments, when the optical device group 200 emits an optical signal, the optical device group 200 may include the light emitting element.

As another example, when the optical device group 200 receives an optical signal, the optical mode size converter 400 may adjust the optical mode size of the optical signal transmitted to the optical device group 200 through the waveguide 322 such that the optical mode size of the optical signal is closer to the optical mode size of the optical device group 200. In embodiments, when the optical device group 200 receives an optical signal, the optical device group 200 may include the light receiving element.

Accordingly, the optogenetic neural probe device 10 according to embodiments of the present disclosure may reduce optical coupling loss using the optical mode size converter 400.

In some embodiments, based on the optical neural probe substrate 310 being located at a lowermost side of the waveguide 322, the optical mode size converter 400 may be located above the core portion 322a or the cladding layer 322b. For example, when the optical neural probe substrate 310 is considered to be located at the lowermost side of the waveguide 322, the optical mode size converter 400 may be located at an uppermost side of the waveguide 322.

The optical mode size converter 400 may include SiN, SiO_2$, SiON, a polymer, PDMA, SU-8, parylene, and the like. In some embodiments, the material of the optical mode size converter 400 may be a material having a refractive index that is different from a refractive index of the core portion 322a or the cladding layer 322b. However, the material of the optical mode size converter 400 is not limited to the specific examples described above.

The optical mode size converter 400 may be configured in a tapered shape, which may refer to a shape having a first side opposite a second side, wherein the first side is larger than the second side, and wherein the shape decreases in size from the first side to the second side. For example, the tapered shape may be a trapezoidal shape. However, embodiments are not limited thereto, and in some embodiments the optical mode size converter 400 may be configured in various shapes different from the tapered shape, examples of which are described below.

On the waveguide 322, there may be provided an optical signal input/output port 323 which may input and output optical signals to and from the outside of the waveguide 322. For example, the optical signal input/output port 323 may be made of, or may include, a diffraction grating. As another example, the optical signal input/output port 323 may be, or may include, a mirror surface, such as a 45-degree mirror surface, which may cause the optical signal to be converted to propagate in a direction perpendicular to its original direction of travel. In FIGS. 1A and 1B, the optical signal input/output port 323 is illustrated as being present at an end of the waveguide 322, but the location of the optical signal input/output port 323 is not limited thereto. For example, the optical signal input/output port 323 may be formed at a location other than the end of the waveguide 322. The optical signal input/output port 323 may be made of, or may include, a diffraction grating and thus may change the direction of light transmitted through the waveguide 322. For example, the optical signal input/output port 323 may change the direction of light to propagate in a direction perpendicular to the waveguide 322. The optical signal input/output port 323 may output the direction-changed light to the outside of the waveguide 322. As another example, the optical signal input/output port 323 may receive external light (e.g., a neural response fluorescent signal or light emitted from an optical device or optical fiber) and input the external light into the waveguide 322. In the examples illustrated in FIGS. 1A and 1B, the optical signal input/output port 323 may be integrated at the end of each core portion 322a. As shown in FIGS. 1A and 1B, the width of the protrusion 321 of the optical neural probe substrate 310 may be narrowed from a particular portion to enable or assist insertion into biological tissue, and a portion of the protrusion 321 which is to be placed adjacent to the nerve cell may have a sharp or sharpened structure, for example the probe peak portion 321a. The probe peak portion 321a may facilitate insertion of the shank 320 into tissue such as nervous tissue or other biological tissue. A portion of the protrusion 321 of the optical neural probe substrate 310 that is to be inserted into biological tissue may have a thinner thickness in comparison with other portions of the optical neural probe substrate 310 by removing a part of the substrate. In embodiments, the optical neural probe substrate 310 may include a recess structure 315 (as shown in FIG. 2A) having a same height as a part of the optical device 210 which contacts the waveguide 322 (or a part of the optical device 210 which contacts the optical mode size converter 400). When the probe 300 includes a plurality of shanks 320, each of the shanks 320 may be arranged and spaced apart by a particular distance. As another example, based on the structure of the nervous tissue, a plurality of shanks 320 included in the probe 300 may be spaced apart at different or varying intervals. In addition, each of the shanks 320 may include one or more optical signal input/output ports 323.

FIGS. 2A and 2B are side views illustrating an embodiment of an optogenetic neural probe device and an optogenetic neural probe having a plurality of inputs and outputs according to embodiments.

Referring to FIG. 2A, the optogenetic neural probe device 10 according to an embodiment may have an extended form in which a plurality of optical neural probe substrates 310 are arranged in a direction perpendicular to the optical device alignment substrate 100. For example, the optogenetic neural probe device 10 may be configured such that a plurality of optical neural probe substrates 310 that are parallel to each other are coupled to a single optical device alignment substrate 100.

In other words, the optogenetic neural probe device 10 may be configured such that a plurality of probes 300 are mounted on an optical device alignment substrate 100. In embodiments, the plurality of probes 300 may have the same structure, some of the plurality of probes 300 may have different structures, or all of the plurality of probes 300 may have different structures. For example, the number of shanks 320 included in each probe 300, the interval between the shanks 320, and the presence or absence or the structure of the optical switches 330 may vary. As another example, the plurality of shanks 320 included in the optogenetic neural probe device 10 may have the same or different structures.

For example, the number or location of the waveguides 322 and the optical signal input/output ports 323 of each shank 320 may be different for each shank 320. In some embodiments, the number or location of the optical mode size converters 400 disposed in the optogenetic neural probe device 10 may also be different for each probe 300 or shank 320.

Referring to FIG. 2A, the optical device alignment substrate 100 may be coated with a fixing resin 500 to vertically fix the optical neural probe substrate 310. For example, the fixing resin 500 may be, or may include, a thermosetting resin, such as spin-on glass (SOG) or benzocyclobutene (BCB), or a photocurable resin, such as UV-epoxy, polydimethylacrylamide (PDMA), SU-8, or a photocurable polymer. However, the type of fixing resin 500 is not limited to the specific examples described above.

As shown in FIG. 2A, an end of the optical neural probe substrate 310 that is closest to the optical device alignment substrate 100 may be in direct contact with the optical device 210. In addition, because the optical device 210 may be integrated with a structure having a particular height on the optical device alignment substrate 100, coupling between the optical device alignment substrate 100 and the optical neural probe substrate 310 may be facilitated by the recess structure 315 having a step at the end of the optical neural probe substrate 310 which is equal to the height of the optical device 210.

Figure 3:
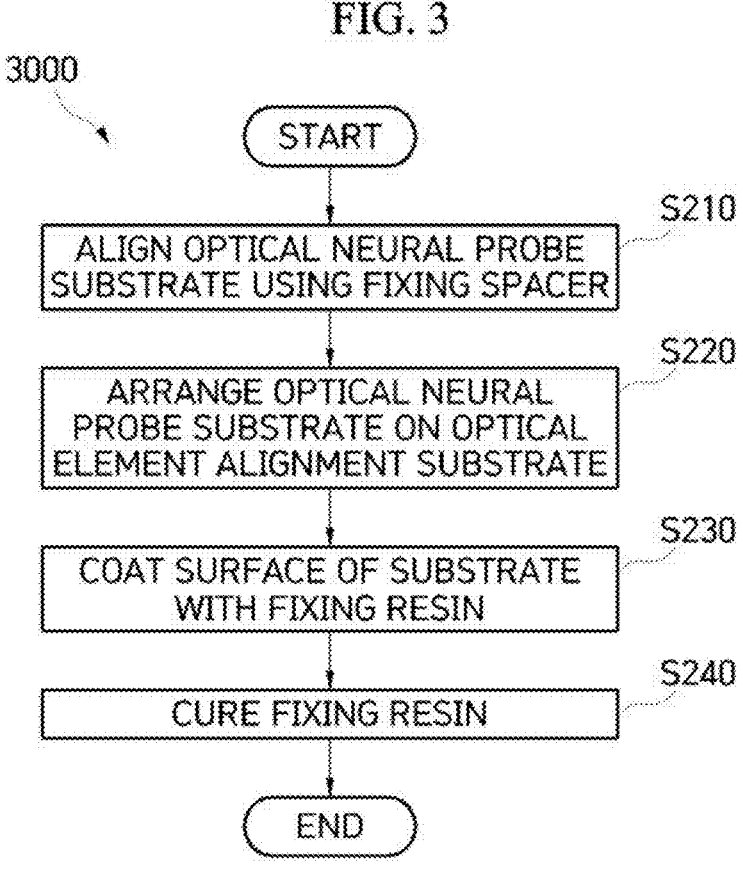
FIG. 3 is a flowchart for describing a method of manufacturing an optogenetic neural probe device having a plurality of inputs and outputs according to an embodiment.

FIG. 3 is a flowchart for describing a process for manufacturing an optogenetic neural probe device having a plurality of inputs and outputs according to an embodiment. The process 3000 for manufacturing an optogenetic neural probe having a plurality of inputs and outputs according to an embodiment may include operations S210 to S240. In embodiments, operations of the process 3000 are not limited to those illustrated in FIG. 3, and some operations may be added, changed, or deleted as needed.

Figure 4A:
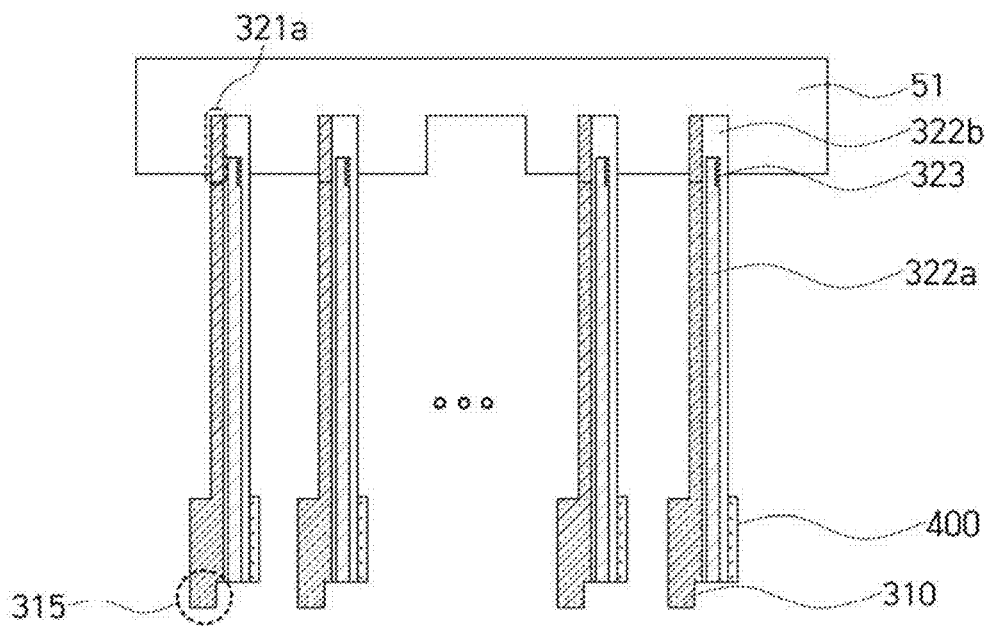
FIGS. 4A to 4C are reference diagrams for describing the method of manufacturing an optogenetic neural probe device having a plurality of inputs and outputs, according to embodiments.
Figure 4A:
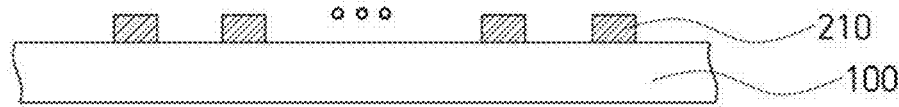
Figure 4B:
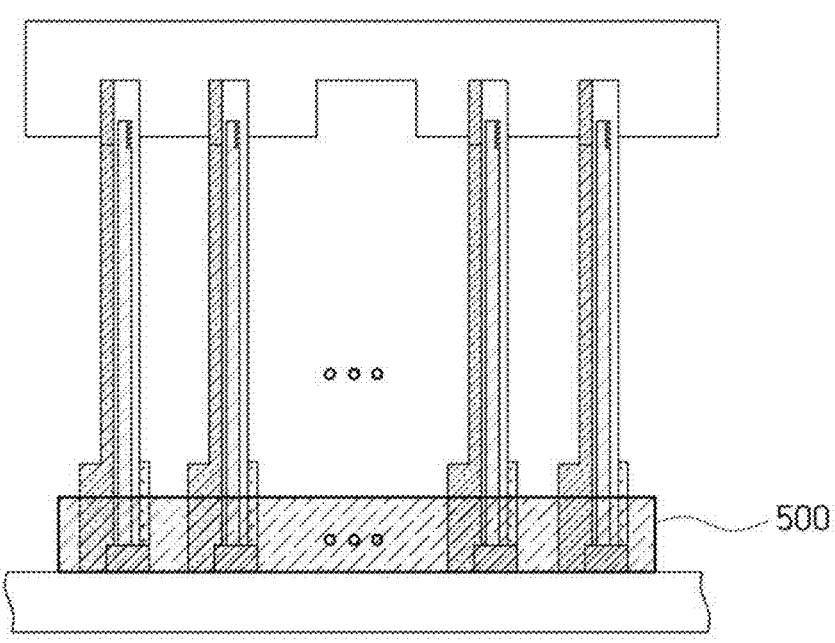
Figure 4C:
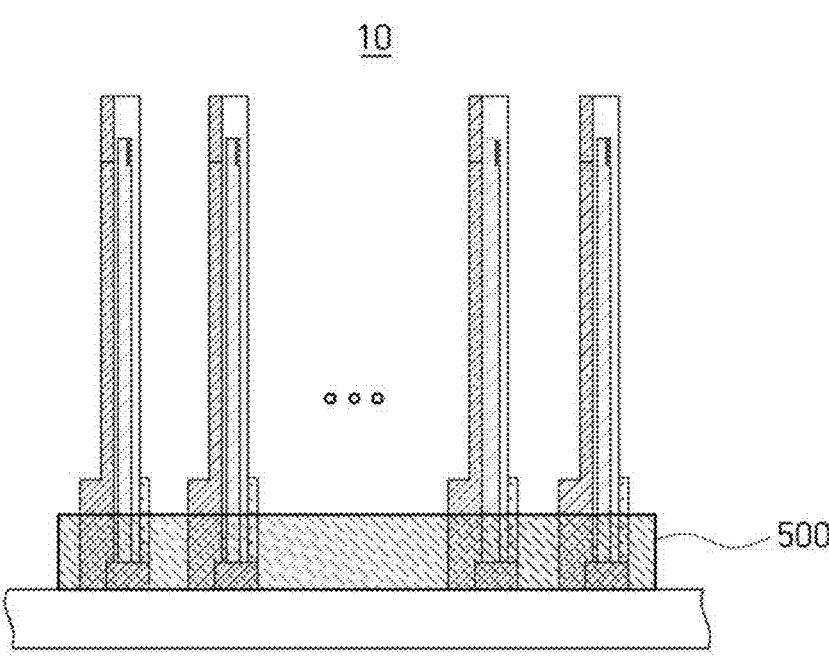

FIGS. 4A to 4C are reference diagrams for describing the process for manufacturing an optogenetic neural probe device having a plurality of inputs and outputs according to an embodiment. Referring to the sequence of FIGS. 4A to 4C, a process of packaging the probe 300 on the optical device alignment substrate 100 on which the optical device 210 is disposed is shown.

Hereinafter, the process of manufacturing an optogenetic neural probe having a plurality of inputs and outputs according to embodiments is described below with reference to FIGS. 3 and 4A to 4C.

As shown in FIGS. 3 and 4A, at operation S210 of the process 3000 may include arraying or aligning the optical neural probe substrate 310 using a fixing spacer 51.

Referring to FIG. 4A, the waveguide 322, the optical signal input/output port 323, and the optical mode size converter 400 may be disposed on the optical neural probe substrate 310. Therefore, operation S210 may also include arraying a plurality of probes 300 using the fixing spacer 51.

First, the optical neural probe substrate 310 to be packaged may be fixed to the fixing spacer 51. The fixing spacer 51 may be used to array the plurality of optical neural probe substrates 310 at an interval which may be same as an interval at which the optical devices 210 are arranged on the optical device alignment substrate 100. The fixing spacer 51 may allow the plurality of optical neural probe substrates 310 to be spaced a particular distance from each other and arrayed and fixed. Accordingly, the recess structure 315 at the end of the optical neural probe substrate 310 may facilitate the coupling of the optical device alignment substrate 100 and the optical neural probe substrate 310 (as shown for example in FIG. 4A).

In some embodiments, before operation S210, the process 3000 may include an operation of arranging a plurality of optical device groups 200 including two or more optical devices to be spaced a particular distance from each other on the optical device alignment substrate 100.

As further shown in FIG. 3, at operation S220 the process 3000 may include arranging the optical neural probe substrate 310 on the optical device alignment substrate 100. When the plurality of optical neural probe substrates 310 are arrayed through the fixing spacer 51, the plurality of optical neural probe substrates 310 may be disposed on the optical device alignment substrate 100 (as shown for example in FIG. 4B). Operation S220 may also be referred to as an operation of positioning the plurality of probes 300 on the optical device alignment substrate 100. As described above with reference to FIG. 2A, the optical neural probe substrate 310 may have a recess structure 315 at one end thereof. At operation S220, the recess structure 315 of the optical neural probe substrate 310 may be placed in contact with the optical device group 200 and the optical device alignment substrate 100, thereby facilitating the coupling of the optical neural probe substrate 310 and the optical device alignment substrate 100.

As further shown in FIG. 3, at operation S230 the process 3000 may include coating a portion of the optogenetic neural probe device 10 with a fixing resin. When all of the plurality of optical neural probe substrates 310 are disposed in physically correct positions, portions of the surface of the optical device alignment substrate 100, with which the optical neural probe substrates 310 are brought into contact, may be coated with a liquid fixing resin 500. The fixing resin 500 shown in FIG. 4B may represent a curable resin before curing.

As further shown in FIG. 3, at operation S240 the process 3000 may include curing the fixing resin. The fixing resin 500 may firmly fix the optical device alignment substrate 100 and the optical neural probe substrate 310 through a curing process. For example, operation S240 may include coupling the optical device alignment substrate 100 and the optical neural probe substrate 310 through the curing of the fixing resin 500. In other words, operation S240 may be considered an operation of coupling the optical device alignment substrate 100 and the probe 300 through curing of the fixing resin 500. The fixing resin 500 shown in FIG. 4C may represent a curable resin after curing (as shown for example in FIG. 4C).

The process for manufacturing the optogenetic neural probe device with the plurality of inputs and outputs is described above with reference to the flowchart presented in the drawing. While the above process is shown and described as a series of blocks for simplicity, it is to be understood that embodiments are not limited to the order of the blocks, and that some blocks may be executed in a different order from those shown and described herein or executed concurrently with other blocks, and various other branches, flow paths, and sequences of blocks that achieve the same or similar results may be implemented. In addition, some illustrated blocks may not be used in some implementations of the method described herein.

In the description above with reference to FIGS. 3 to 4C, each operation may be further divided into a larger number of sub-operations or combined into a smaller number of operations according to embodiments. In addition, some of the operations may be omitted or may be performed in reverse order as needed. In addition, even in the case of omitted content, the content of FIG. 1A, FIG. 1B, FIG. 2A, FIG. 2B, FIG. 5A to FIG. 5D, and FIG. 6 may be applied to the content of FIGS. 3 to 4C. In addition, the content of FIGS. 3 to 4C may be applied to the content of FIG. 1A, FIG. 1B, FIG. 2A, FIG. 2B, FIGS. 5A to 5D, and FIG. 6

FIGS. 5A to 5D are exemplary diagrams illustrating various types of optical mode size converters. In FIGS. 5A to 5D, various types of optical mode size converters 400 that may be included in the optogenetic neural probe device 10 according to embodiments are illustrated. Various types of optical mode size converters 400 may be applied to the optogenetic neural probe device 10 to minimize optical coupling loss under given conditions. Specifically, various types of optical mode size converters 400 may be applied to the optogenetic neural probe device 10 depending on the number of optical devices 210 included in the optical device group 200, the optical mode size of light emitted from the optical device 210, and the manufacturing process or manufacturing technology level of the optical mode size converter 400.

Figure 5A:
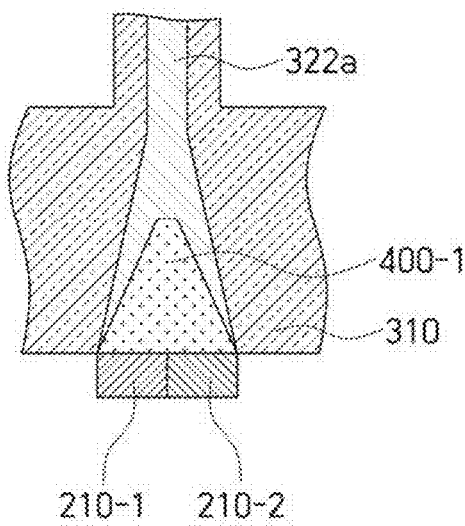
FIGS. 5A to 5D are exemplary diagrams illustrating various types of optical mode size converters, according to embodiments.

FIG. 5A shows a tapered optical mode size converter 400-1, which may be referred to as a basic type. The tapered optical mode size converter 400-1 may be one example of a basic optical mode size converter 400. The tapered optical mode size converter 400-1 may be suitable for use in many different application types due to its relatively simple manufacturing process and relatively simple design and operating principles.

Figure 5B:
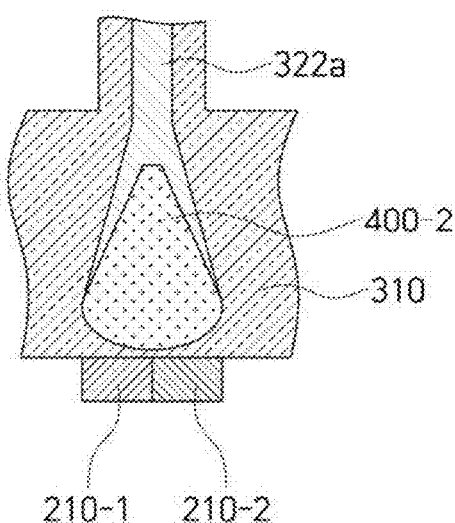

FIG. 5B shows a single-lens optical mode size converter 400-2, which may be rounded at one end, and may include a single lens shape. The single-lens optical mode size converter 400-2 may reduce optical loss through condensation when light emitted from the optical device 210 has a large radiation angle in the horizontal direction. However, the single-lens optical mode size converter 400-2 may require relatively advanced optical calculations during design, and due to the need to form a curved pattern in the production thereof, may have limitations in being applied unless a manufacturing process or manufacturing technology for implementing a fine pattern is used.

Figure 5C:
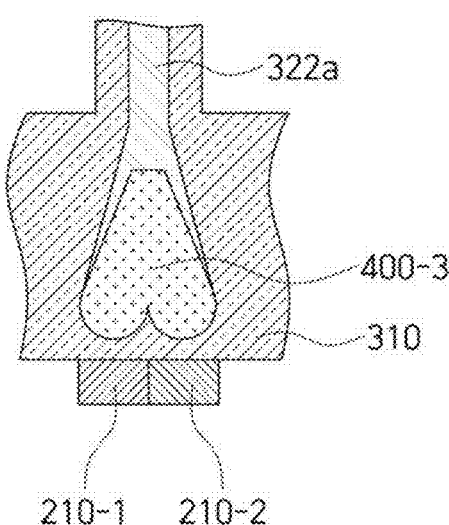

FIG. 5C shows a multiple-lens optical mode size converter 400-3 having a plurality of lens shapes. The multiple-lens optical mode size converter 400-3 shown in FIG. 5C has a shape with one lens corresponding to each optical device 210. For example, the multiple-lens optical mode size converter 400-3 shown in FIG. 5C is an optical mode size converter that has one lens for each optical device. The multiple-lens optical mode size converter 400-3, which may have one lens for each optical device, may be an improvement over the single-lens optical mode size converter 400-2, and when the plurality of optical devices 210 are present on the optical device alignment substrate 100, total optical coupling efficiency may be enhanced by optimizing the curvature of each lens included in the multiple-lens optical mode size converter 400-3 to correspond to the characteristics of each optical device 210. However, because the radius of the lenses may be smaller than the lens of the single-lens optical mode size converter 400, a manufacturing process or manufacturing technology capable of producing a finer pattern may be required.

Figure 5D:
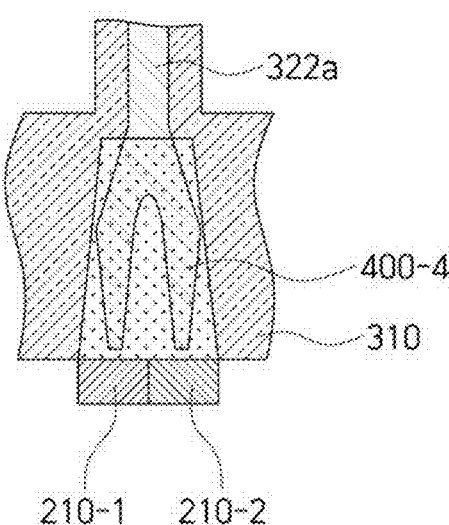

FIG. 5D shows an inverse-tapered optical mode size converter 400-4 including an inverse-tapered waveguide. For example, to correspond to the optical devices 210, the inverse-tapered optical mode size converter 400-4 may include one inverse-tapered waveguide for each optical device 210. In addition, the inverse-tapered optical mode size converter 400-4 may include a structure similar to the tapered optical mode size converter 400-1 on an upper side of the inverse-tapered waveguide in a direction perpendicular to the optical neural probe substrate 310. The inverse tapered optical mode size converter 400-4 may exhibit a high optical coupling loss improvement effect when the optical mode size of light emitted from the optical device 210 is large in the vertical direction. For example, when the optical mode size is large in the vertical direction, mode matching may be achieved using the inverse tapered waveguide, thereby allowing coupling of the waveguide 322 while reducing loss. However, because the inverse tapered optical mode size converter 400-4 may require a narrow waveguide width on the side closer to the optical device 210, the pattern width required for manufacturing the inverse-tapered optical mode size converter 400-4 may have a smaller area than the pattern width required for manufacturing the tapered optical mode size converter 400-1. In embodiments, the narrow waveguide width of the inverse-tapered portion of the inverse-tapered optical mode size converter 400-4 may be set to be as narrow as possible during the manufacturing process.

The optical mode size converter 400 may be implemented in various ways other than those shown in FIGS. 5A to 5D.

Figure 6:
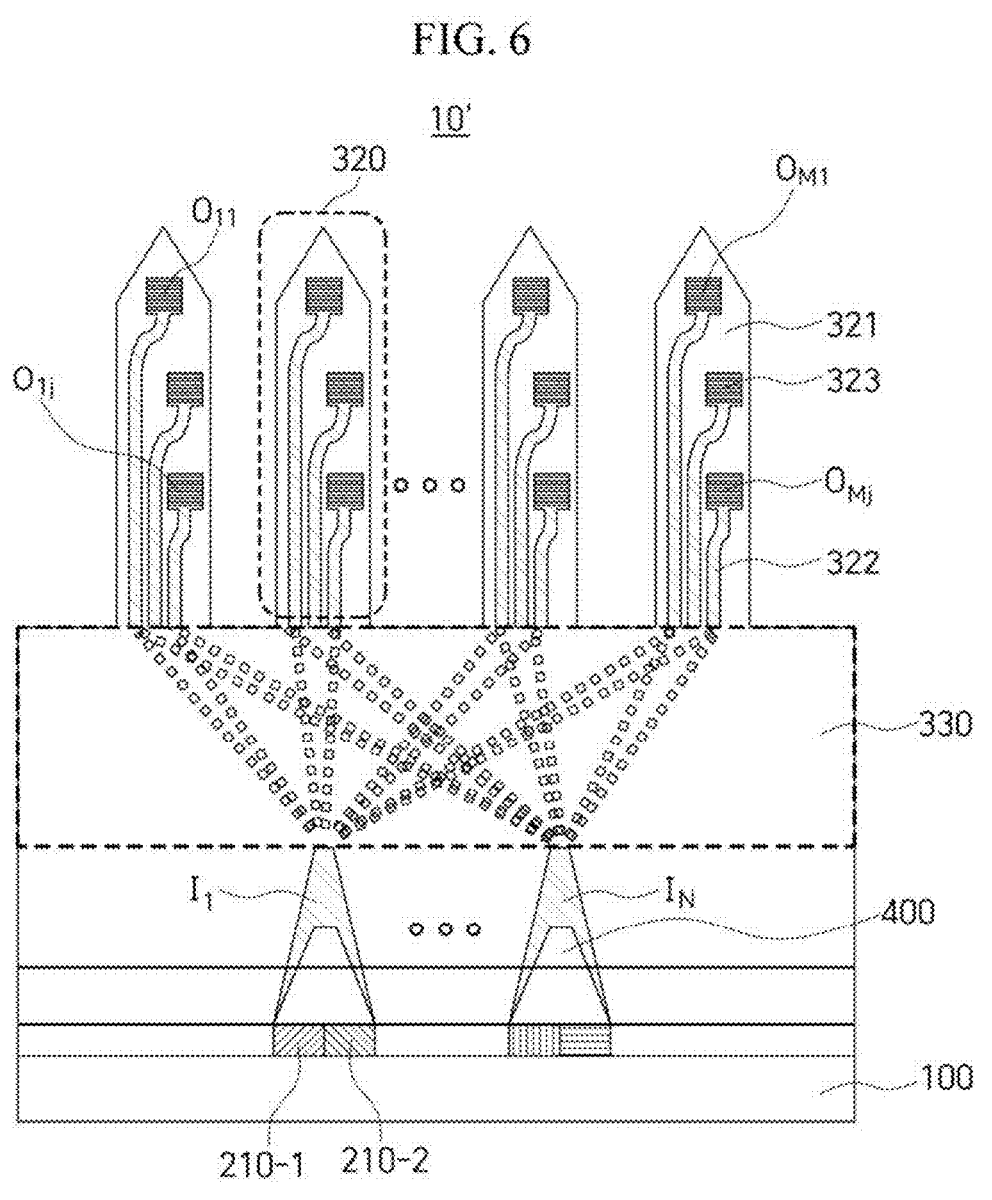

FIG. 6 is an exemplary diagram illustrating a form of an optogenetic neural probe having a plurality of inputs and outputs according to embodiments, which includes an optical switch.

As shown in FIG. 6, the optogenetic neural probe device 10' may include a probe 300 including an optical switch 330. The optogenetic neural probe device 10' may further include the optical switch 330 in the probe 300 described above. Referring to FIG. 6, the optical switch 330 may be disposed between the optical mode size converter 400 and the plurality of waveguides 322.

In the example shown in FIG. 6, the optical signal input/output port 323 is illustrated as being disposed at the end of the waveguide 322, however as described above, the optical signal input/output port 323 may be disposed at any position on the waveguide 322. For example, the optical signal input/output port 323 may be disposed at the end of the waveguide 322, but may also be disposed at a part other than the end of the waveguide 322.

As shown in FIG. 6, in some embodiments a plurality of optical signal input/output ports 323 may be disposed on a single waveguide 322. According to embodiments, one shank 320 may include a plurality of waveguides 322, or only one waveguide 322.

In embodiments, the optical switch 330 included in a particular probe 300 may be referred to as an N×(M×j) switch (where "x" denotes a multiplication sign). As shown in FIG. 6, each of the shanks 320 may have the same number j of optical signal input/output ports 323. However, it should be understood that the optogenetic neural probe device 10' according to some embodiments may include a different number of optical signal input/output ports 323 for each shank 320. In embodiments N may refer to the number of optical device groups 200, M may refer to the number of shanks 320, and j may refer to the number of optical signal input/output ports 323 arranged in each shank 320. Because the number of optical device groups 200 may be N, the number of optical mode size converters 400 may also be N.

In the optogenetic neural probe device 10' including N optical device groups 200, M shanks 320, and j optical signal input/output ports 323 for each shank 320 as described above, an optical switch 330 may be used to control the connection between the N optical device groups 200 and the M×j optical signal input/output ports 323 included in the probe 300. As shown in FIG. 6, each of the M×j optical signal input/output ports 323 may be identified by symbols $O_{11}, \ldots, O_{1j}, \ldots, O_{M1}, \ldots,$ and $O_{Mj}$.

For example, when the optogenetic neural probe device 10' transmits an optical signal emitted from the optical device group 200 to the optical signal input/output port 323, the input $I_1$ and the input $I_N$ may have different wavelengths of optical signals, and the effects of each wavelength on nerve cells may be different between the wavelengths. The optogenetic neural probe device 10' may transmit each optical signal to the optical signal input/output port 323, which is the target point of the optical signal, through the optical switch 330. For example, the optical switch 330 may be a device that implements switching of optical signals. To this end, the probe 300 may be manufactured in a form in which the N×(M×j) optical switches 330 are integrated. For example, the optical switch 330 may be implemented using various functional elements, such as a phased-array, an arrayed waveguide grating (AWG), a Mach-Zehnder interferometer (MZI), a ring resonator, or a directional coupler, and other methods.

As an example, when the optical device 210 disposed on the optical device alignment substrate 100 is a light source that generates an optical signal, the optical signal from the optical device 210 may pass through the optical switch 330 and reach the optical signal input/output port 323 that is the target point.

As another example, when the optical device 210 is a light receiving element (an optical receiver) that converts an optical signal into an electrical signal, a fluorescent signal generated from a nerve cell may be received in the waveguide 322 through a particular optical signal input/output port 323, and the fluorescence signal may be transmitted to the optical device 210 through the optical switch 330.

In some embodiments, the optogenetic neural probe device 10' may include an optical switch driving circuit or an optical device driving circuit. The optical switch driving circuit may be electrically connected to the optical switch to control the operation of the optical switch. The optical device driving circuit may be electrically connected to the optical device to control the operation of the optical device 210. The optical switch driving circuit or the optical device driving circuit may be mounted on a substrate included in the optogenetic neural probe device 10', or may be manufactured on a separate substrate and additionally mounted.

The optogenetic neural probe device 10' illustrated in FIG. 6 may enable routing of optical signals emitted from the optical device 210, which is not possible in the optogenetic neural probe device 10 according to the embodiment shown in FIG. 1A, through the optical switch 330, and reduce the number of optical devices 210.

As is apparent from the above, an optogenetic neural probe device according to an embodiment of the present disclosure may have an independent optical device array chip as a base to achieve physical separation between an optical device, such as a light source generating heat, and biological tissue, thereby preventing damage to the biological tissue due to heat.

In addition, the optogenetic neural probe device according to an embodiment of the present disclosure may use an optical signal input/output method that employs a probe array based on optical waveguide technology having structural scalability in design and manufacturing, and thus may have an effect of being applicable to research of neural tissue having a three-dimensional volume.

In addition, the optogenetic neural probe device according to an embodiment of the present disclosure may allow installation of various optical mode size converters, thereby reducing the optical loss that occurs in the process of combining the optical device array chip and the optical neural probe chip.

Additionally, the optogenetic neural probe device according to an embodiment of the present disclosure may provide a multiple switch area within the optical neural probe, thereby reducing the number of optical devices in comparison with the number of input and output stages.

In embodiments, a process for manufacturing an optogenetic neural probe device according to an embodiment of the present disclosure may use a recessed region structure for coupling a three-dimensional probe array, thereby enabling ease of optical coupling and alignment with the optical device array chip.

The effects of the present disclosure are not limited to those described above, and other effects that are not described above will be clearly understood by those skilled in the art from the above detailed description.

Although some embodiments have been described in detail above with reference to the drawings, those of ordinary skill in the technical field to which the present disclosure pertains will understand that various modifications and alterations may be made without departing from the technical spirit or features of the present disclosure.

What is claimed is:

1. An optogenetic neural probe device comprising:
an optical device alignment substrate;
an optical device group on the optical device alignment substrate, the optical device group comprising one or more optical devices; and
one or more optogenetic neural probes, wherein each optogenetic neural probe from among the one or more optogenetic neural probes comprises an optical neural probe substrate, an optical waveguide on the optical neural probe substrate, and an optical signal input/output port,
wherein the optogenetic neural probe is configured to transmit an optical signal emitted from the optical device group to the optical signal input/output port through the optical waveguide,
wherein the optogenetic neural probe further comprises an optical mode size converter, the optical mode size converter being provided between at least one optical device of the optical device group and the optical waveguide, and
wherein a cross-sectional area of the optical mode size converter decreases in a direction from the at least one optical device toward the optical signal input/output port.

2. The optogenetic neural probe device of claim 1, wherein the optical device group comprises a first optical device and a second optical device, and
wherein a central wavelength characteristic of the first optical device is different from a central wavelength characteristic of the second optical device.

3. The optogenetic neural probe device of claim 1, wherein the optical device group comprises a first optical device and a second optical device, and
wherein the first optical device comprises a light emitting element, and the second optical device comprises a light receiving element.

4. The optogenetic neural probe device of claim 1, wherein the optical signal input/output port is configured to receive a fluorescent signal from a nerve cell, and to transmit the fluorescent signal to the optical waveguide, and
wherein the optical waveguide is configured to transmit the fluorescent signal to the optical device group.

5. The optogenetic neural probe device of claim 1, wherein the optical neural probe substrate is packaged on one side of the optical device alignment substrate.

6. The optogenetic neural probe device of claim 5, wherein the optical neural probe substrate directly contacts the optical device group at a portion of the optical neural probe substrate that is packaged on the optical device alignment substrate,
wherein the portion comprises a recess structure including a step, and
wherein a height of the step is equal to a height of the optical device group.

7. The optogenetic neural probe device of claim 5, wherein the optical device alignment substrate is coated with a fixing resin such that the optical neural probe substrate is fixed to the optical device alignment substrate.

8. The optogenetic neural probe device of claim 7, wherein the fixing resin comprises at least one from among a thermosetting resin and a photocurable resin.

9. The optogenetic neural probe device of claim 1, wherein the optogenetic neural probe comprises a plurality of shanks,
wherein each shank from among the plurality of shanks comprises a protrusion of the optical neural probe substrate, the optical waveguide, and the optical signal input/output port, and
wherein the plurality of shanks are spaced apart from each other at a predetermined interval.

10. The optogenetic neural probe device of claim 9, wherein at least one shank from among the plurality of shanks comprises a plurality of optical signal input/output ports on the optical waveguide included in the at least one shank.

11. The optogenetic neural probe device of claim 9, wherein at least one shank from among the plurality of shanks comprises a plurality of optical waveguides.

12. The optogenetic neural probe device of claim 1, wherein the optical signal input/output port is disposed at an end of the optical waveguide.

13. The optogenetic neural probe device of claim 1, wherein the optical signal input/output port comprises a diffraction grating.

14. The optogenetic neural probe device of claim 1, wherein the optical signal input/output port comprises a 45 degree mirror surface.

15. The optogenetic neural probe device of claim 1, wherein the optical device group comprises a plurality of optical device groups.

16. The optogenetic neural probe device of claim 1, wherein the optical mode size converter has one lens for each optical device, and a curvature of the one lens is determined by characteristics of a corresponding optical device.

* * * * *